(12) United States Patent
Cocola et al.

(10) Patent No.: US 9,193,985 B2
(45) Date of Patent: Nov. 24, 2015

(54) DEVICE AND METHOD FOR MICROBIOLOGICAL ANALYSIS OF BIOLOGICAL SAMPLES

(75) Inventors: Francesco Cocola, Siena (IT); Michele Meloni, Siena (IT)

(73) Assignee: DIESSE DIAGNOSTICA SENESE S.p.A., Milan (IT)

( * ) Notice: Subject to any disclaimer, the term of this patent is extended or adjusted under 35 U.S.C. 154(b) by 760 days.

(21) Appl. No.: 12/746,241

(22) PCT Filed: Dec. 4, 2008

(86) PCT No.: PCT/IT2008/000743
§ 371 (c)(1),
(2), (4) Date: Jun. 21, 2010

(87) PCT Pub. No.: WO2009/072161
PCT Pub. Date: Jun. 11, 2009

(65) Prior Publication Data
US 2010/0255529 A1    Oct. 7, 2010

(30) Foreign Application Priority Data
Dec. 7, 2007   (IT) ................ FI2007A0275

(51) Int. Cl.
C12Q 1/04    (2006.01)
G01N 35/02    (2006.01)
G01N 35/04    (2006.01)

(52) U.S. Cl.
CPC ............ C12Q 1/04 (2013.01); G01N 35/026 (2013.01); *G01N 2035/0406* (2013.01); *G01N 2035/0484* (2013.01)

(58) Field of Classification Search
None
See application file for complete search history.

(56) References Cited

U.S. PATENT DOCUMENTS

| 4,073,691 | A | * | 2/1978 | Ahnell et al. ............... 435/34 |
| 4,713,345 | A |   | 12/1987 | Ramsden |
| 4,971,900 | A |   | 11/1990 | Ahnell et al. |
| 5,094,955 | A |   | 3/1992 | Calandra et al. |
| 5,155,019 | A |   | 10/1992 | Sussman et al. |
| 5,217,876 | A |   | 6/1993 | Turner et al. |
| 5,482,842 | A | * | 1/1996 | Berndt ....................... 435/34 |
| 5,814,474 | A | * | 9/1998 | Berndt ....................... 435/34 |
| 5,856,175 | A |   | 1/1999 | Thorpe et al. |
| 6,709,857 | B2 |   | 3/2004 | Bachur, Jr. |
| 6,872,291 | B2 | * | 3/2005 | Boyd et al. ................ 204/472 |
| 7,141,213 | B1 | * | 11/2006 | Pang et al. ................. 422/65 |
| 2002/0197708 | A1 |   | 12/2002 | Bachur, Jr. |

FOREIGN PATENT DOCUMENTS

EP    1 398 043 A2    3/2004
WO    WO 99/50646    10/1999

OTHER PUBLICATIONS

Thorpe et al. "BacT/Alert: an automated colorimetric microbial detection system". Journal of Clinical Microbiology, 1990, vol. 28, No. 7, pp. 1608-1612.*
F. Gardini et al.; "A head space gas chromatographic approach for the monitoring of hte microbial cell activity and the cell viability evaluation" Journal of Microbiological Methods, 29 (1997) 103-114.

* cited by examiner

*Primary Examiner* — Vera Afremova
(74) *Attorney, Agent, or Firm* — McGlew and Tuttle, P.C.

(57) ABSTRACT

The device for microbiological analyzes on samples of body fluids comprising: an incubation area for containers containing said samples; an analyzer for analyzing the inner atmosphere of said containers; a sorting system to sort the containers according to the carbon dioxide content detected by said analyzer.

11 Claims, 12 Drawing Sheets

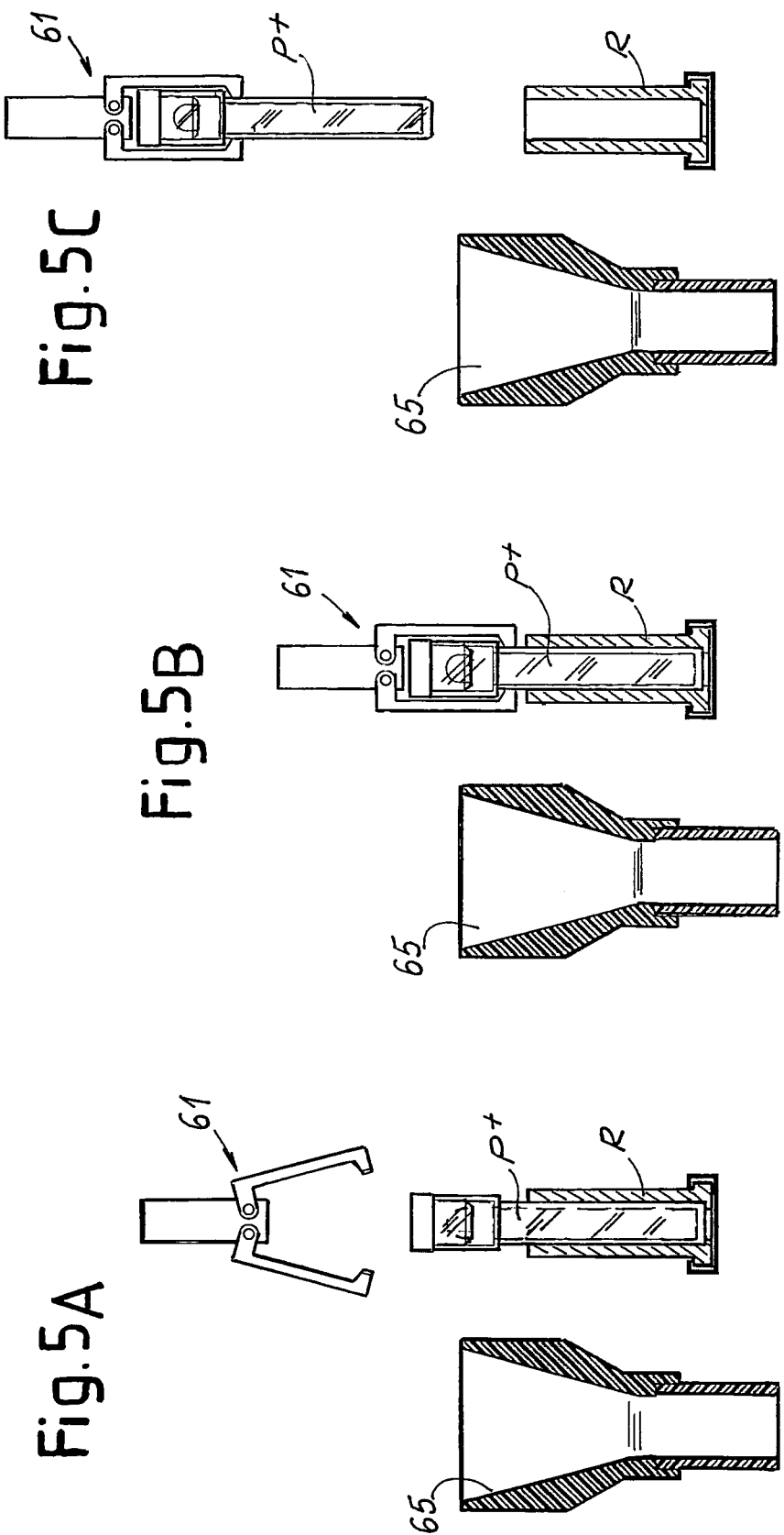

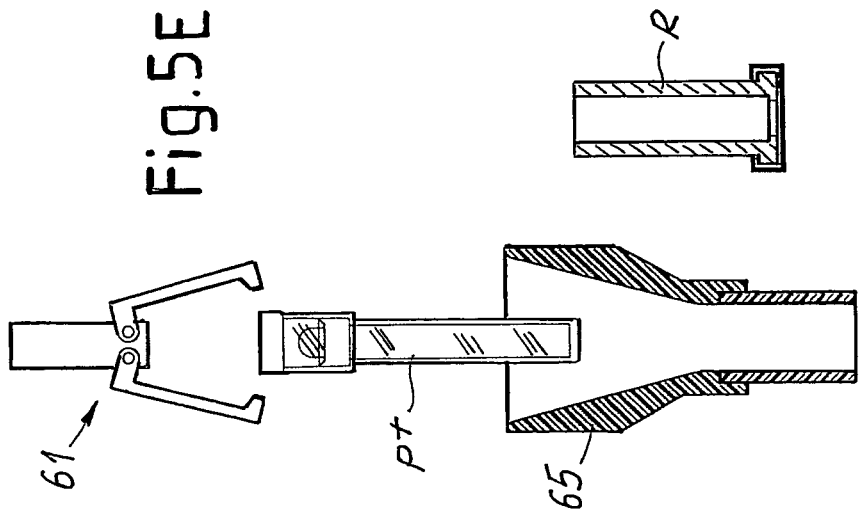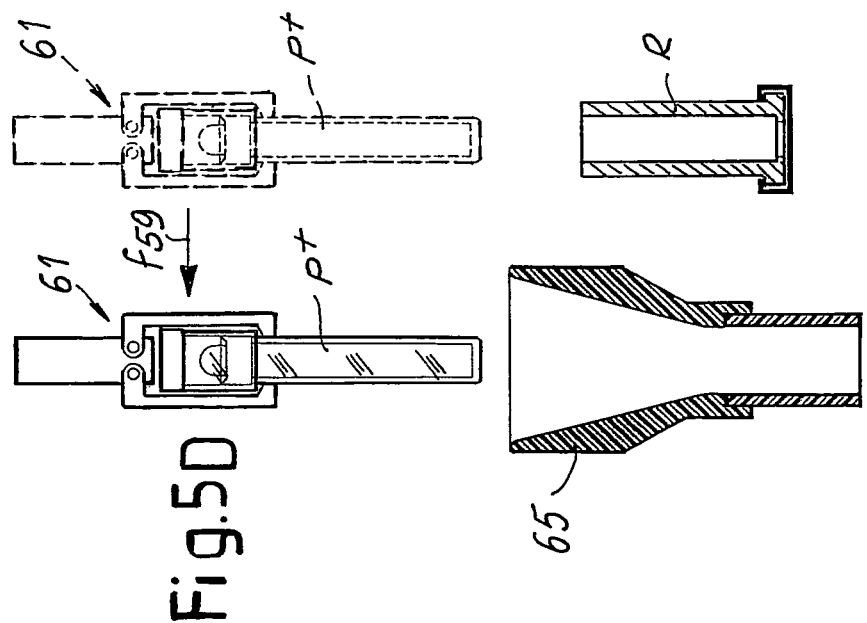

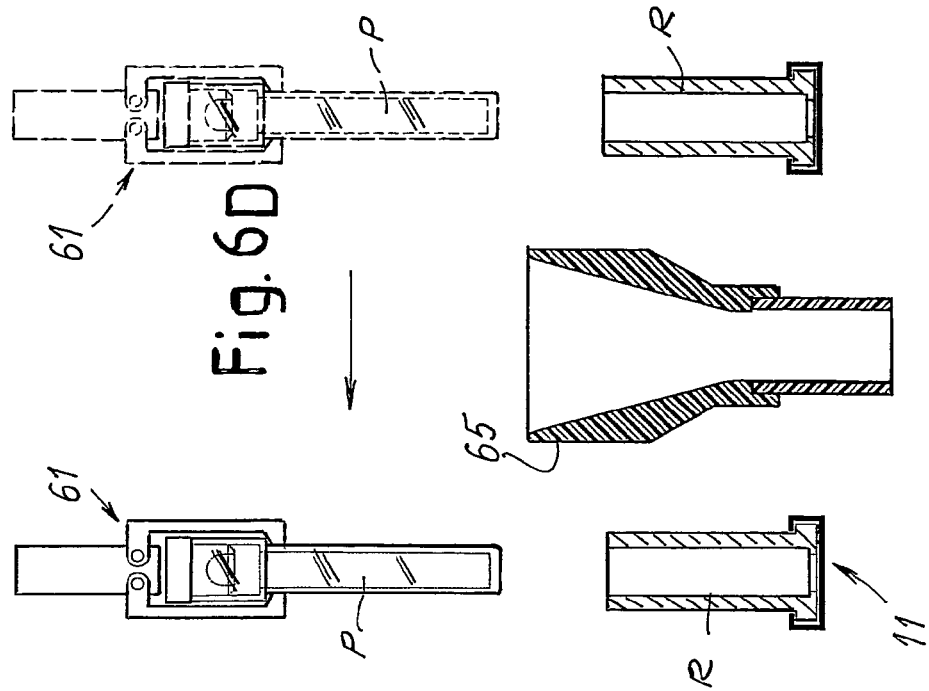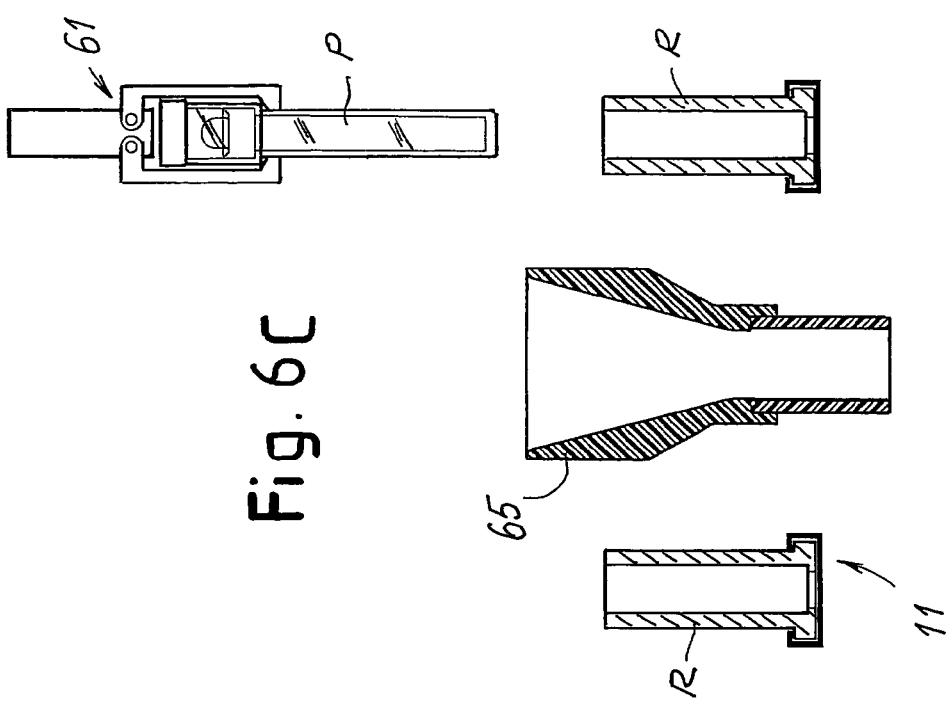

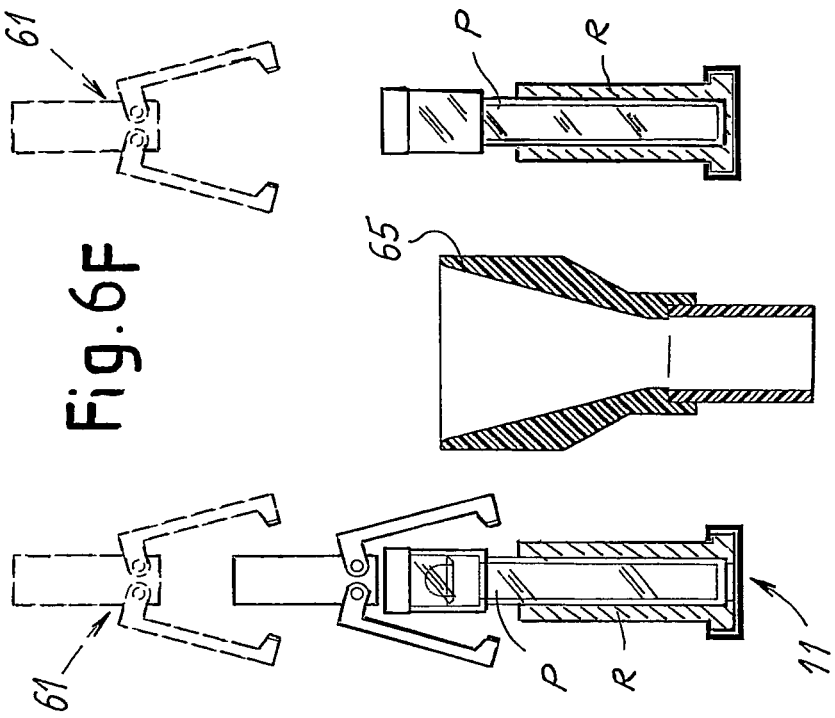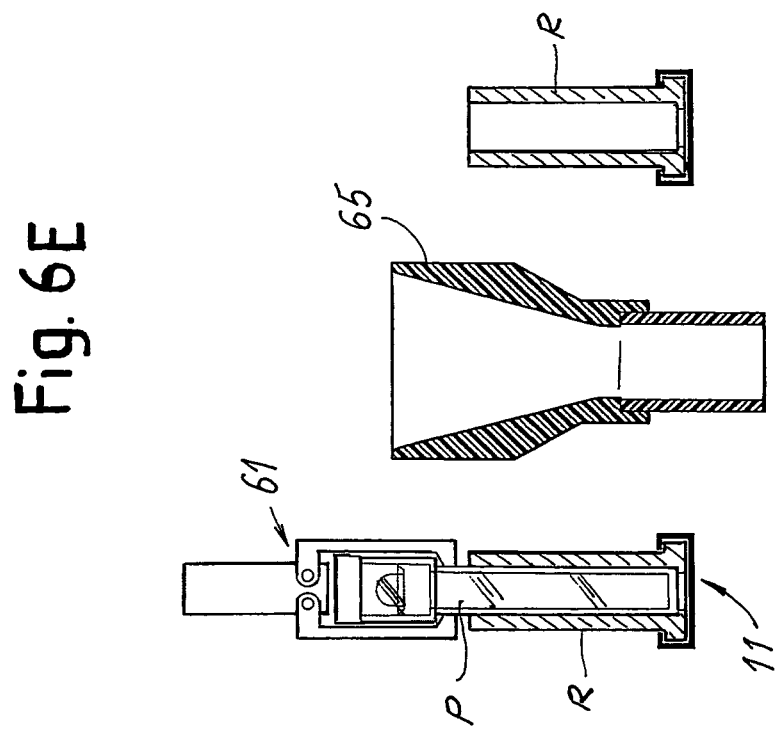

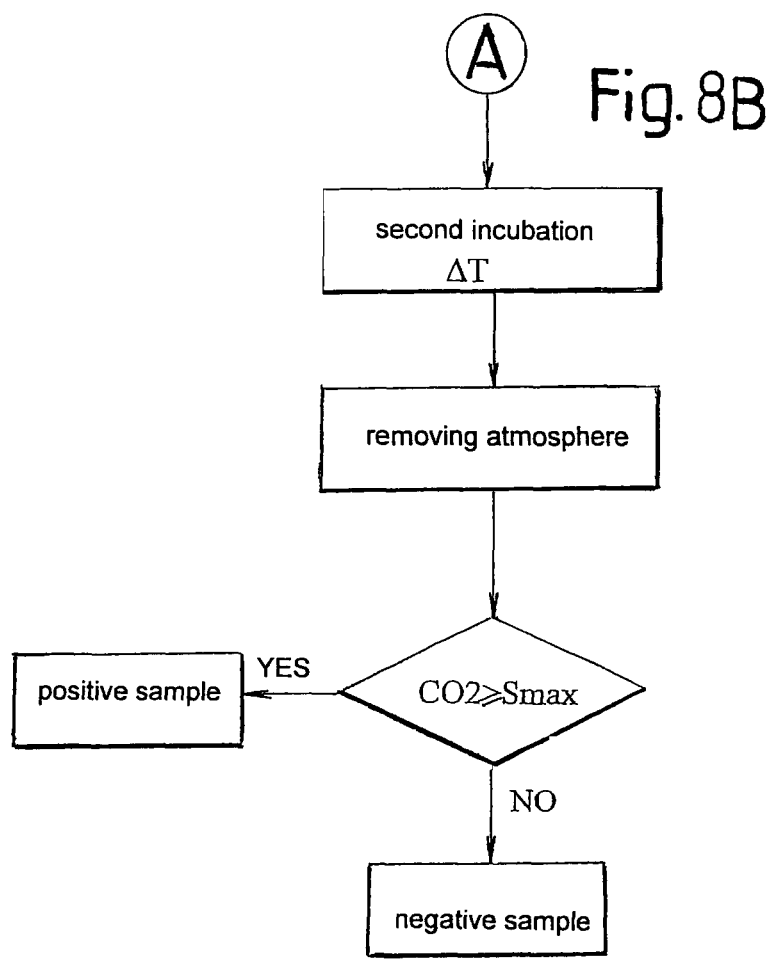

DEVICE AND METHOD FOR MICROBIOLOGICAL ANALYSIS OF BIOLOGICAL SAMPLES

TECHNICAL FIELD

The present invention relates to methods and devices to perform analyses of biological samples, and more in particular microbiological analyses aimed at verifying the presence of bacteriologically significant concentrations of microorganisms inside biological samples, such as in particular, although not exclusively, samples of body fluids, such as urine and blood.

STATE OF THE ART

The performance of microbiological analyses on biological samples, in particular body fluids, is well known, in order to verify the presence of pathogenic agents, generally microorganisms that can have a harmful effect on the health of humans or animals. This type of analyses is usually carried out on urine, blood, feces and buffers. In general, verifying the presence of pathogenic agents inside the sample is not sufficient, and it is also necessary to classify them, i.e. to verify what type of microorganism is involved, in order to check its harmfulness to the health and to prescribe the necessary treatments.

The traditional methods for microbiological analysis of urine samples are based upon the so called seeding, which provides for the distribution of the sample to be analyzed on a growth medium, leaving it there for a high number of hours (typically 12 hours or more), in order to verify whether microorganism colonies grow on the medium or not. If so, these microorganisms are examined in order to check the nature thereof.

When more samples must be analyzed, the seeding process is extremely long lasting, and requires some preparation by the operator who performs it. Handling a high number of samples entails biological risks, as well as risks linked to the possibility of confusing the samples with each other, thus wrongly attributing the analysis results to the patients.

In F. Gardini et al. "*A head space gas chromatographic approach for the monitoring of the microbial cell activity and the cell viability evaluation*" Journal of Microbiological Methods, 29 (1997) 103-114, an approach is described based upon the gas chromatography to detect the microbial activity inside the samples to be analyzed. The gas chromatography aims at identifying the carbon dioxide ($CO_2$) concentration present in the atmosphere in which the sample is, and whose presence is due to the metabolism of the microorganisms present in the sample. This approach requires complex and expensive equipment, as well as long analysis times.

U.S. Pat. No. 4,971,900 describes a method and a device for the detection of biologically active agents in samples of various nature, for example also urine. The method is based upon the analysis of the carbon dioxide content in the atmosphere above the sample, which is positioned on the growth medium. The analysis lasts many hours, and aims at identifying any pathogenic agent by means of the trend of carbon dioxide development over time. This analysis method requires extremely long times and is not particularly reliable as the detection of the microorganism depends upon the correct tracing of the time curve of the carbon dioxide development. In particular, problems may arise when pathogenic agents of different type are present inside the sample, which develop according to times different from each other.

U.S. Pat. No. 6,709,857 describes a system for optically detecting the gas concentration in a vial containing a sample to be analyzed. The gas concentration is detected by means of photothermal spectroscopy.

U.S. Pat. No. 5,155,019 describes a method for detecting the presence of biological activity in a sample utilizing an infrared analysis of the sample sealed in a container, in order to identify the presence and the concentration of carbon dioxide in the atmosphere above the sample cultured inside the container. In this case again, particularly long times are required for the analysis, as well as a complex equipment.

U.S. Pat. No. 5,217,876 describes a method for detecting the presence of microorganisms in a sample inside a container. The method is based upon the idea of optically detecting a change in the color of an indicator medium in the container in which the sample is cultured, change that is due to the development of carbon dioxide because of the presence of a microbiological activity inside the sample. In this case again, long times are required for the analysis and, as in the previously mentioned case, the identification of the pathogenic agent present in the sample is not particularly reliable, as it is based upon the trend of the carbon dioxide development over time.

A similar method is described in U.S. Pat. No. 5,094,955.

U.S. Pat. No. 5,482,842 describes a further method for detecting microorganisms within body fluids, in particular a blood sample. The analysis is carried out through an infrared light source and an infrared detector. In this case again, the presence of carbon dioxide is detected, which develops due to the presence of pathogenic microorganisms. Carbon dioxide has an infrared radiation absorption coefficient different from that of the atmosphere normally present (in the absence of pathogenic agents) above the level of the sample inside the vial.

U.S. Pat. No. 5,856,175 describes a device for the detection of pathogenic agents in samples of body fluids, which is similar to the device described in U.S. Pat. No. 5,094,955 and in U.S. Pat. No. 5,217,876.

U.S. Pat. No. 5,814,474 describes a device for the direct detection of microorganisms in culture bottles. The described device is used for the analysis of samples of urine, saliva or blood. Substantially, the method described herein is based upon the analysis of the atmosphere contained in the vial inside which the cultured sample is inserted. The gas inside the vial is made pass through gas sensors in order to detect the composition thereof and then to identify, based upon the result of the gas analysis, the microorganisms present in the sample. This analysis method is particularly complex, requires very expensive sensors and long analysis times.

SUMMARY OF THE INVENTION

According to one aspect, the present invention provides for a method that simplifies and accelerates the operations for the analysis of body fluids, in particular but not exclusively urine. According to some embodiments, the method according to the present invention allows to distinguish, in a plurality of samples, the surely positive samples from the surely negative ones, i.e. to distinguish the samples inside which at least one pathogenic agent is present, which must be identified in a second more accurate analysis phase, from the sample surely devoid of pathogenic agents, for which it is therefore useless to perform further analyses.

In this way, during the subsequent phase of analysis of the samples, which can be carried out through a seeding process or other known process, only some of the originally considered samples are treated, whilst the surely negative samples do not require further processing.

According to one embodiment, the method according to the present invention comprises the following steps:
a) introducing a biological sample to be analyzed in a test tube containing a growth medium;
b) incubating the test tube for a first time interval;
c) analyzing, following the first time interval, the atmosphere in said test tube;
d) determining, based upon the carbon dioxide quantity detected in the atmosphere, whether the biological sample contains a pathologically relevant bacterial load or not.

The present invention is substantially based upon the idea of using the carbon dioxide quantity detected in the atmosphere inside a sample not for identifying the type of pathogenic agent, which may be present in the sample, as in the traditional methods, but as a parameter to distinguish surely negative samples from the surely positive ones. The identification of the type of pathogenic agent present in the positive samples will be carried out in a subsequent more accurate analysis phase, e.g. a seeding process, or other known systems, for example described in the patent documents mentioned in the introductory part of the present description. However, the only methods that currently allow to identify in a reliable manner the type of microorganisms present in the samples are those based upon the seeding, characterized by the drawbacks described above.

In one embodiment of the present invention, it is possible to provide for two threshold values, with which the carbon dioxide content that develops after a given time inside each single container of cultured sample is compared. In some embodiments it is possible to provide for the samples, whose carbon dioxide content after the preset incubation time interval is greater than a first limit value, to be classified as surely positive, and vice versa for the samples that after the same incubation period present a carbon dioxide content lesser than a second lower limit value, to be classified as surely negative. The intermediate samples can be considered uncertain and, for greater reliability of the analysis, they can be subjected to a detailed analysis in order to verify the presence and the type of microorganisms.

Vice versa, according to a modified embodiment of the present invention, the uncertain samples, instead of being subjected to a detailed analysis, for example to a seeding process, can be subjected to a second incubation interval, renewing the atmosphere present in the single containers of the samples, if necessary. This renewal of the atmosphere allows to eliminate the carbon dioxide presence and to add oxygen in order to develop the metabolism of the microorganisms present in the sample, if any. After a second incubation time interval, the uncertain samples are subjected again to a verification of the carbon dioxide content in the atmosphere of the container. This content is then compared with a threshold value, which distinguishes between surely positive samples (for which the carbon dioxide content is greater than the threshold value) and surely negative samples, for which the carbon dioxide content is lesser than the threshold value.

Through this second operating method it is possible further to reduce the samples that must be subjected to the subsequent seeding process, as the samples, which have been determined as uncertain through the first analysis phase, are further subdivided into surely positive samples and surely negative samples. These latter are not subjected to seeding or other analysis process in order to determine the type of pathogenic agents contained inside them.

Further advantageous embodiments and possible features of the method according to the present invention are indicated in the appended claims and will be described in greater detail hereunder with reference to one embodiment.

According to a different aspect, the present invention relates to a device for microbiological analyses of samples of body fluids, such as urine or the like, comprising:
an incubation area for containers containing said samples;
an analyzer for analyzing the inner atmosphere of said containers;
a sorting system to sort the containers according to the carbon dioxide content detected by said analyzer.

Substantially, in some embodiments the device provides for an incubation area, where the samples contained inside the single containers are incubated for an adequate period of time, for example of around one hour. The samples are then analyzed through the analyzer, and sorted, i.e. subdivided into positive samples and negative samples. In an improved embodiment the sorting system subdivides the samples that have been subjected to this first incubation into surely positive samples, surely negative samples and uncertain samples. The device can present a second incubation area for the uncertain samples, where they stay for a second incubation time interval, if necessary following the renewal of the atmosphere inside their containers due to the above described reasons. It is also possible for the second incubation phase to be carried out in the incubation area, where the first incubation of the single samples occurs. The equipment will be adequately controlled by a microprocessor, so that it can store in a memory information relating to the position of the containers with the samples that are performing the first incubation phase and the samples that are performing the second incubation phase, so as to avoid errors in the execution of the first and of the second incubation phase of the various samples contained inside the analysis equipment or device.

Further advantageous features and embodiments of the device according to the present invention are indicated in the appended dependent claims and shall be described in greater detail with reference to a non-limiting embodiment of the invention.

According to a further aspect, a further object of the present invention is to provide a test tube for the analysis method and for use with the equipment according to the present invention. More in particular, according to one embodiment the test tube of the present invention is a vacuum test tube containing a growth medium suitable to the development of microorganisms that may be present in the specific biological sample to which the test tube is destined, as well as a magnetic agitating element located inside the test tube.

BRIEF DESCRIPTION OF THE DRAWINGS

The invention will be better understood by following the description below and the attached drawing, which shows a non-limiting practical embodiment of the invention. More in particular, in the drawing:

FIGS. 5A and 5E show the sequence of handling of the positive samples.

DETAILED DESCRIPTION OF EMBODIMENTS OF THE INVENTION

Figure 1:
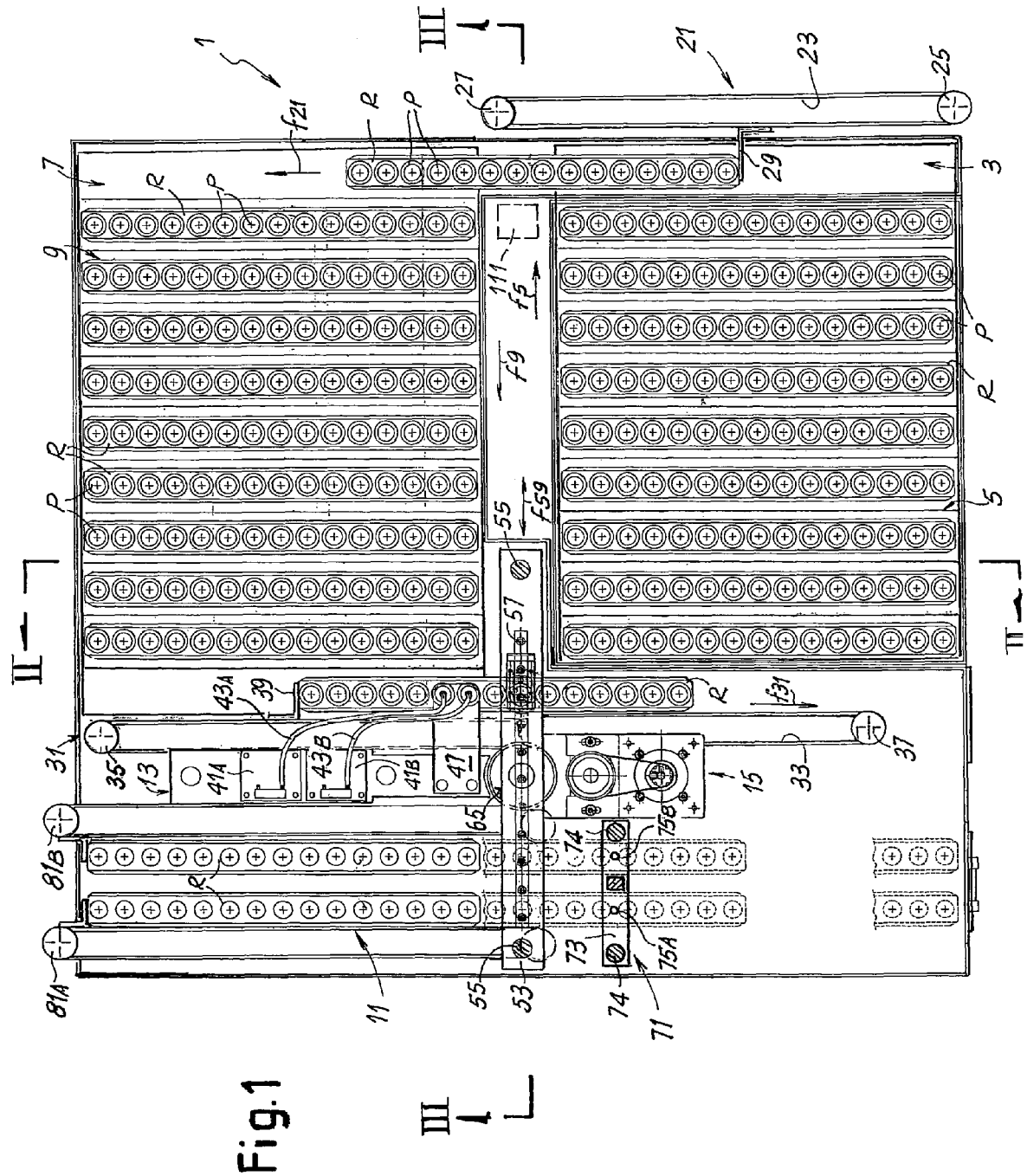
FIG. 1 shows a plan view of a device according to the invention.
Figure 2:
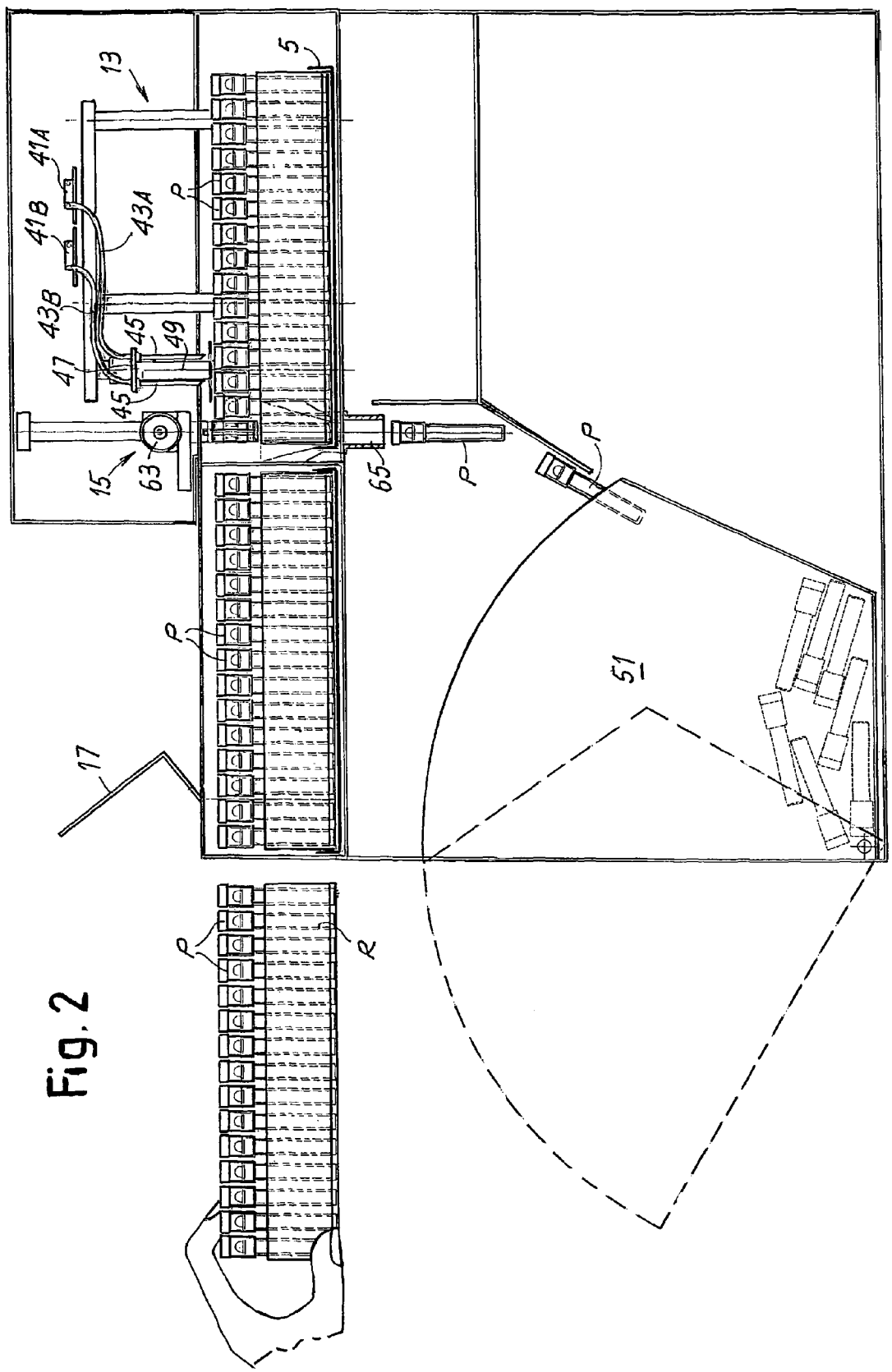
FIG. 2 shows a section according to II-II of FIG. 1.
Figure 3:
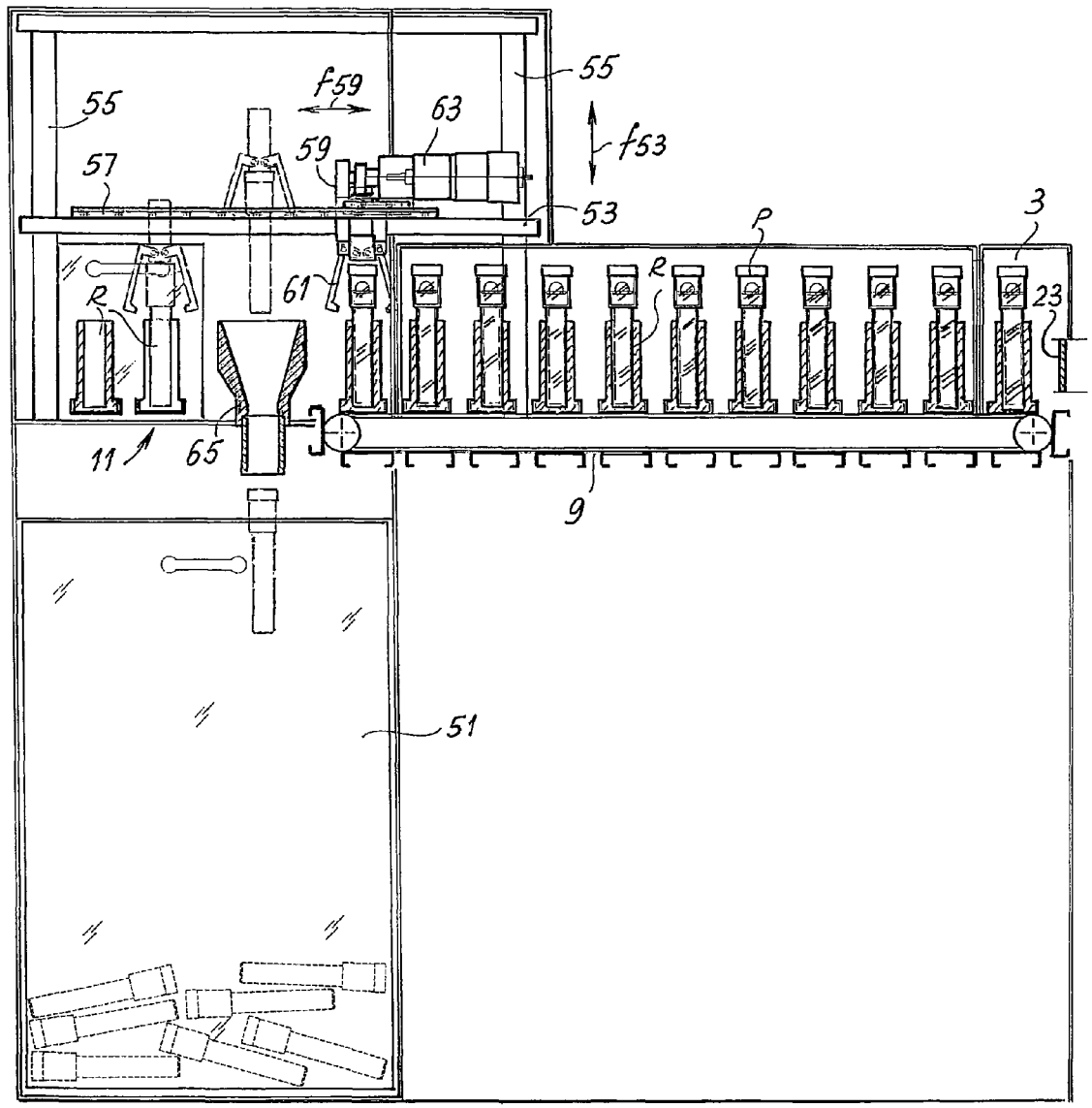
FIG. 3 shows a section according to III-Ill of FIG. 1.

With reference to FIGS. 1 to 3, a device according to the present invention, indicated as a whole with number 1, comprises a loading area 3 for loading racks R of containers P, in which single racks of containers P containing the biological sample to be analyzed are inserted and handled according to the arrow f5 by a first conveyor 5.

In the illustrated embodiment the containers are vacuum test tubes, with a seal cap, but it should be understood that also containers of different type can be used, sealed in order to detect, if necessary, the accumulation of carbon dioxide inside them due to the metabolism of microorganisms, if any, which are contained in the sample and develop thanks to a growth medium contained inside the test tube where the sample is positioned.

Adjacent to the load area 3, an incubation area 7 is provided, where a second conveyor 9 is arranged, which moves the racks R of test tubes P according to the arrow f9.

The number 11 generally indicates a rest area for test tubes P, preferably housed in a rack R, containing uncertain samples that must be subjected to a second incubation. Between the incubation area 7 and the rest area 11 an analyzer, indicated as a whole with the number 13, and a sorter, indicated as a whole with the number 15, are arranged. The analyzer performs in sequence on the single test tubes P of the racks R coming from the incubation area 7 the analysis of the atmosphere contained inside the test tubes. Based upon the result of the analysis performed by the analyzer 13, the sorter 15 sorts the test tubes, subdividing them into test tubes containing positive samples, i.e. samples on which an analysis must be performed to identify the pathogenic microorganisms contained in the sample, and test tubes containing negative samples, i.e. on which a further analysis is not required, as they do not contain significant pathogenic agents, and lastly test tubes containing uncertain samples which are carried to the rest area 11 in order to be subjected to a second incubation phase.

With specific reference to the loading area 3, single racks R, containing test tubes P in which samples to be analyzed are arranged, are inserted inside it through an aperture closed by a door 17 (FIG. 2). The conveyor 5 transfers in a stepped manner the single racks R from the position of insertion in the load area 3 towards a transferring unit 21, which transfers the single racks R of test tubes P from the loading area 3 to the incubation area 7. In some embodiments the transferring unit 21 comprises a continuous flexible member 23 driven around pulleys 25, 27, at least one of which is motorized. To the flexible member 23 one or more pushers 29 are fixed, which push the single racks R containing the test tubes P in order to handle them according to the arrow f21 in a direction orthogonal with respect to the feed direction f5 of the conveyor 5. The transferring unit can also assume different configurations, for example it can comprise a threaded rod, to which a cursor with a pusher is engaged. The rotation of the rod in a direction and in the opposite direction causes the feed and the return of the cursor and the related pusher.

Whichever configuration has the transferring unit 21, it provides to transfer the single racks R containing the test tubes P of samples to be analyzed from the loading area 3, which can be maintained at a low temperature in order to inhibit or to slow down the metabolism of the microorganisms, if any, present in the samples, to the incubation area 7, preferably maintained at a controlled temperature, for example around 37° C.

In the incubation area 7 the conveyor 9 moves in a stepped manner the single racks R with the test tubes P from the position, in which they are inserted from the transferring unit 21 to the incubation area 7, towards an analyzing and sorting area, where the analyzer 13 and the sorter 15 are arranged.

In the analyzing and sorting area a second transferring unit 31 is provided, similar to the transferring unit 21 and comprising for example a flexible member 33 driven around pulleys 35, 37. To the flexible member 33 one or more pushers 39 are constrained, which push with a stepped controlled movement the single racks R towards a sorter. The transferring unit 31 is controlled by a programmable electronic control unit, not shown, in such a way as to feed each rack R in a stepped manner according to the arrow f31, taking it off from the conveyor 9 and passing individually the single test tubes P contained in the rack R through the analyzer 13. In this way, each test tube can be analyzed by aspirating a sample of the atmosphere contained inside it and determining the carbon dioxide content which has developed in the test tube due to the effect of the metabolism of the pathogenic microorganisms, if any, which can be contained inside the sample cultured in the test tubes P during the incubation period in the incubation area 7.

The incubation has a modest duration with respect to the incubation times used in the traditional analysis systems, and lasts for example about one hour, the convey 9 being programmed to move with such a speed that the incubation time is substantially equal to the time a single rack needs to pass from the position where the transferring unit 21 is located, to the position where the transferring unit 31 is located.

Figure 4:
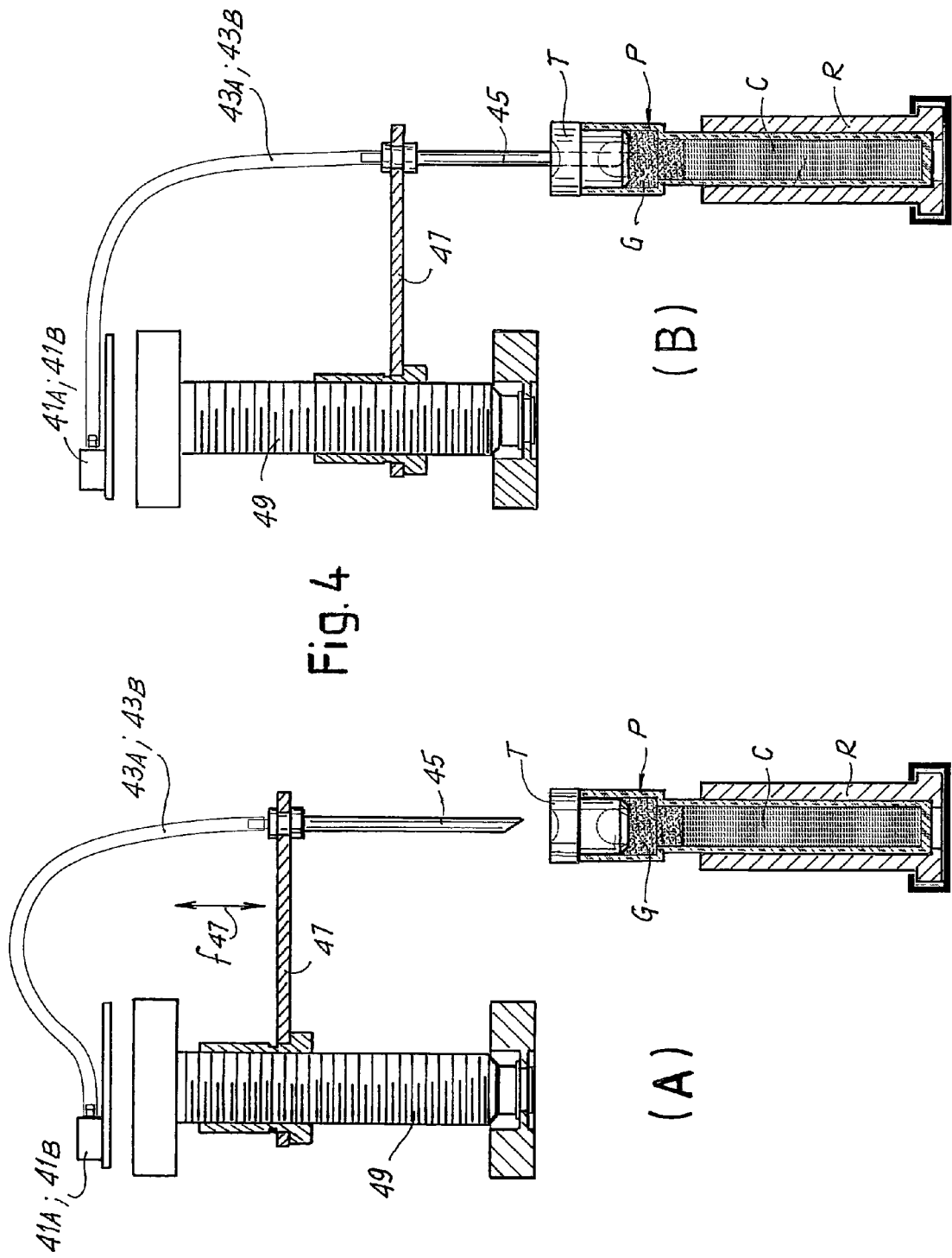
FIGS. 4A and 4B show a detail of the analyzer and of the system of cannulas or needles for the removal of the atmosphere from the single containers of the samples.

As shown in particular also in FIG. 4, in this embodiment the analyzer is double, and comprises a first sensor 41A and a second sensor 41B, realized to determine with a sufficient precision the carbon dioxide content inside the single test tubes P. With this double arrangement it is possible to double the speed of analysis of the device. Each sensor 41A, 41B can be made in NDIR technique, as described for example in U.S. Pat. No. 6,255,653, whose content is incorporated in the present description by reference. Each sensor is connected through a respective flexible duct 43A, 43B to a pervious needle 45, one of which is visible in FIG. 4. The two needles 45 are carried by a slide 47 vertically sliding along guide columns 49 according to a movement f47 imparted by an actuator, not shown. The lifting and lowering movement of the needles 45 integral with the slide 47 is used to make the two needles 45 penetrate in the test tubes P, which each time are located below the slide 47. The lowering of the needles 45 is controlled in such a manner that the needles remain in the area of the single test tube P, in which is located the gaseous atmosphere, indicated with G in FIG. 4, without touching the biological sample C, e.g. a sample of urine, blood or other body fluid, collected in the lowest part of the test tube P. The lowering movement of the needles 45 causes the perforation of the caps T of the test tubes P, so that a part of the gas above the sample C can flow through the pervious needles 45 and the flexible ducts 43A, 43B, towards the sensors 41A, 41B of the analyzer 13. FIGS. 4A and 4B show the penetration movement of the pervious needles 45 through the caps T of the test tubes P in order to position themselves (FIG. 4B) in the gas aspiration position. The gas in the single test tube P can flow through the respective duct 43A, 43B towards the sensor 41A, 41B due to the effect of the overpressure which generates inside the test tube because of the accumulation of carbon dioxide developed by the metabolism of the microorganisms, if any, present in the sample C.

The sensors 41A, 41B are able to detect the quantity of carbon dioxide present in the single analyzed test tubes with a precision sufficient for the purposes described below. A high precision, as well as a long or repeated detection are not necessary, as instead they are in the traditional systems, where the trend of the carbon dioxide concentration is used as significant parameter to determine the type of microorganism present in the sample. On the contrary, according to the present invention what is important is substantially the presence of carbon dioxide as an index of the metabolism of microorganisms present in the sample, whose nature will be determined, if necessary, in a subsequent phase of qualitative analysis carried out on the positive samples.

On the single test tubes P contained in the racks R the sorter 15 performs operations, which will be described below with specific reference to FIGS. 5 and 6, as a function of the carbon dioxide quantity detected by the single sensors 41A, 41B.

The sorter 15 provides to pick up the single test tubes P from the rack R which is fed in a stepped manner by the transferring unit 31 in order to sort them in the rest area 11, or in a tray 51 below (FIG. 2) where the positive samples accumulate, or also to leave the negative samples in the rack R which is then taken by the operator and emptied of the test tubes P or simply ejected from the analyzing machine for a subsequent handling by the operator.

More in particular, in the illustrated embodiment the sorter 15 comprises a slide 53 guided on substantially vertical guides 55 and provided with a movement according to the double arrow f53 (see in particular FIG. 3). Along the slide 53 a cursor 59 is movable along guides 57, which carries a gripper 61 provided with an opening and closing element controlled by an actuator 63 carried by the cursor 59. The cursor 59 is provided with a movement according to the double arrow f59 (FIG. 3) along the longitudinal development of the slide 53. Thanks to this double movement f59 and f53, the gripper 61 can take single test tubes P from the rack R which is pushed in a stepped manner by the transferring unit 31 in order to discharge them through a well 65 in the space 51 below or to insert them in one or in the other of the two racks R which are in the rest area 11.

It should be understood that the number of racks R in the rest area 11 can be different from that shown. For example, only one rack R can be provided, or more than two racks R, in which case the stroke of the gripper 61 with its cursor 59 in the direction f59 will be obviously extended in an adequate manner so as to reach all the racks R arranged parallel in the rest area 11.

FIGS. 5A-5E show the movement of the gripper 61 to discharge a test tube $P^+$ containing a positive sample (i.e. a sample in which there is such a bacterial load requiring a further analysis, for example through seeding, in order to detect the type of microorganisms present), through the well 65 in the space 51 below. In FIG. 5A the open gripper is lowered towards the test tube $P^+$ which is above the gripper and which was carried in this position through a movement according to f31 of the respective rack actuated by the transferring unit 31. In FIG. 5B the gripper is lowered and is closed to engage the test tube $P^+$. In FIG. 5C the test tube is lifted by extracting the test tube $P^+$ from the rack R so that with a movement according to f59 the test tube is moved above the well 65 (FIG. 5B) where the gripper 61 opens in order to make the test tube $P^+$ fall in the well (FIG. 5E). Through the well, the test tube $P^+$ achieves a collection area, from where the operator will collect all the test tubes, which must be subjected to an analysis according to a known method, in order to detect the types of microorganisms present in the samples contained inside these test tubes.

When the sample in the test tube P which must be picked up by the gripper 61 is negative, i.e. when after the about 1 hour incubation in the incubation area 7 the analyzer 41A or 41B has not detected a significant carbon dioxide content in the atmosphere taken from the upper part of the test tube P, this test tube remains in the rack R and then passes, without being handled by the gripper 61, beyond the position in which the manipulator 15 is located.

Figure 6A:
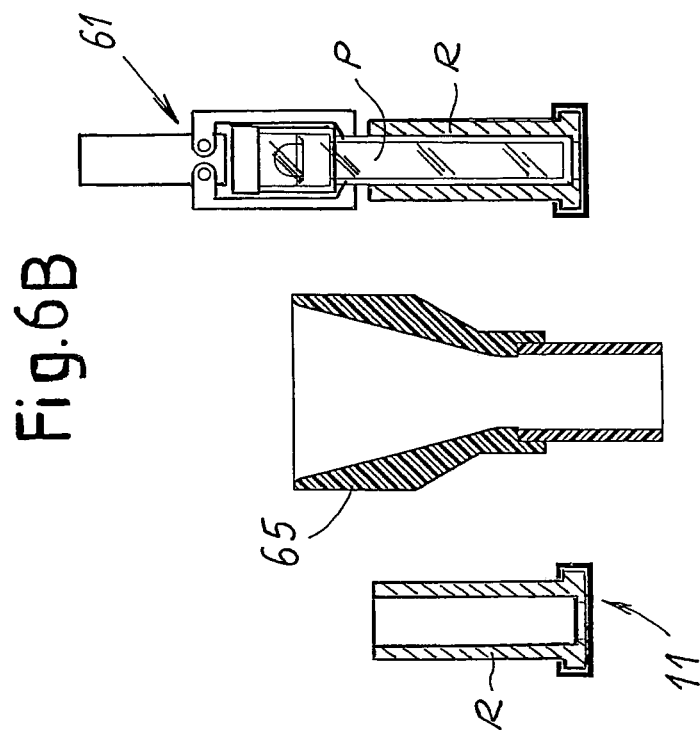
FIGS. 6A and 6F show the sequence of handling of the uncertain samples.
Figure 6B:
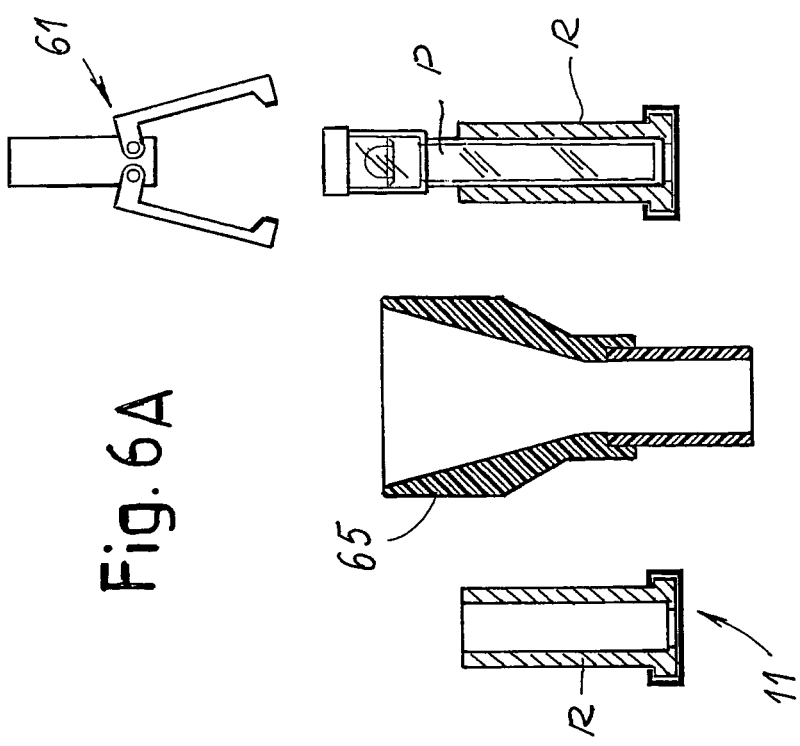

The samples for which in the inner atmosphere of the test tube a carbon dioxide content has been detected which is greater than a minimum value (below which the test tube is considered negative), but lower than a maximum value (over which the test tube is considered positive), are picked up by the gripper 61 and handled according to the cycle schematically illustrated in FIGS. 6A-6E. In FIG. 6A the open gripper is ready to lower on the test tube indicated with $P^?$, which must be subjected to a further incubation. In FIG. 6B the gripper has dropped and closed on the test tube $P^?$. Then the gripper 61 provides to extract according to the arrow f53 the test tube $P^?$ and to transfer it towards one of the racks R, which are in the rest area 11 with a movement which passes beyond the discharge well 65 as shown in FIGS. 6C and 6D. Once achieved this position, the gripper 61 is lowered to insert the uncertain test tube $P^?$ in the rack R of the rest area 11 (FIG. 6E), then it opens and lifts leaving the test tube in the rack, then returning in the gripping position for gripping a new test tube P contained in the rack R, which is fed in a stepped manner by the transferring unit 31 (FIG. 6F).

In this way in the racks R of the rest area 11 accumulate the single uncertain samples contained in the test tubes $P^?$, whose carbon dioxide content is comprised between two rest values, minimum and maximum, and for these samples a further incubation is necessary.

In a modified embodiment, it is also possible to provide for all the uncertain samples to be subjected to a further analysis in order to detect the type of microorganisms contained inside them, thus not providing for the rest area 11, or leaving it inactive and sorting the test tubes simply by subdividing them into positive and negative, thus discharging the uncertain samples according to the procedure described above directly in the well 65 together with the positive samples. It is also possible not to provide for the discharge well, and to transfer the positive and uncertain samples in the area 11, from where they are manually picked up for a seeding process or other procedure for the detection of the pathogenic microorganisms inside them, whilst on the original racks R coming from the first incubation area the test tubes with the surely negative samples remain.

According to further embodiments, it is possible to put the negative samples in the discharge well, so that no test tubes remain on the racks R coming from the incubation area. In a further variant of embodiment, the surely negative samples can be transferred in the rest area 11, the surely positive samples can be discharged through the well in the area below and the uncertain samples can remain in the rack in order to be inserted in the load area again.

What is important is, substantially, the fact that a sorting is carried out at least between positive test tubes and negative test tubes, and preferably between positive test tubes, negative test tubes and uncertain test tubes, these latter being subject to a second incubation phase.

According to some embodiments, in the rest area 11 incubation means can be provided, so that the uncertain test tubes $P^+$ are maintained in conditions of incubation at a controlled temperature, for example about 37° C., directly in the rest area 11 and from here they are handled in the way described above, providing for example a second analyzer in the rest area 11, or transferring the single racks from the rest or second incubation area 11 to the area in which the sensor 41A, 41B are active.

However, according to the preferred embodiment, the racks R, which have been filled in the rest area 11, are picked up by the operator, who inserts them again in the load area 3 so that they can be subjected to a new incubation cycle in the incubation area 7.

In order to allow the uncertain samples contained in the test tubes P (P?) of the rest area 11 to develop the metabolism of the microorganisms present there, according to some embodiments in the rest area 11 a device can be provided, generically indicated with the number 71, which injects oxygen or in any case a gas containing oxygen in the single test tubes P, which are in the rest area 11. The device 71 can comprise for example a slide 73 vertically movable along guide columns 74 and carrying a pair of pervious needles 75A, 75B which can perforate the test tubes P which are in the rest area 11 and insufflate inside them oxygen or ambient air, fed for example by a compressor connected to the needles 75A, 75B by means of flexible ducts. Feeding of the racks R in the rest area 11 in order to allow their filling with the uncertain test tubes P? and their perforation passing through the device 71 is obtained for example through two transferring members 81A, 81B with a conformation substantially equal to that of the transferring units 21, 31 and not described in greater detail.

In this way the single racks R are gradually filled with the uncertain test tubes P? passing below the slide 53 and carry each test tube P below the needles 75A, 75B so as to make the test tubes receive oxygen that can develop the metabolism of the microorganisms and thus push the racks R outside the rest area 11 in order to allow their re-introduction in the load area 3.

The device will be provided with a user interface which allows to communicate to the central unit of the machine which racks R inserted in the load area 3 have already undergone a first incubation phase, and thus contain uncertain test tubes, and which are loaded with new test tubes on which the first incubation in the area 7 must be carried out.

In this way the machine, being provided with encoders associated with all the actuators for handling the racks through the different areas of the machine, can know in any instant what rack contains test tubes already undergone a first incubation and now in phase of second incubation, and what racks contain test tubes which must be subjected to a first incubation, the analysis and a second incubation, if necessary, if the test tubes result to be uncertain. Alternatively, instead of following the single test tubes with a control of the feeding movements, it is possible to provide a system for reading bar codes or other codes associated to the test tubes, to recognize each test tube in the essential points of their path through the machine.

The test tubes containing uncertain samples (test tubes P?) coming from the rest area 11, once they have been subjected to a second incubation phase in the incubation area 7 (or, in a modified embodiment, directly in the rest area 11), are subjected to a new analysis through the analyzer 13. The carbon dioxide content detected during this second analysis is compared preferably with a single threshold value. The samples containing a carbon dioxide quantity greater than the threshold value are considered positive, and thus discharged through the sorter 15 in the well 65, whilst the samples containing a carbon dioxide quantity lower than this threshold value are considered negative and remain in the rack, which is gradually ejected from the area 7 due to the effect of the transferring unit 31.

The threshold used for the discrimination following the second incubation can be equal to the minimum threshold or to the maximum threshold used for sorting and discriminating the test tubes, which underwent a first incubation phase.

Figure 8A:
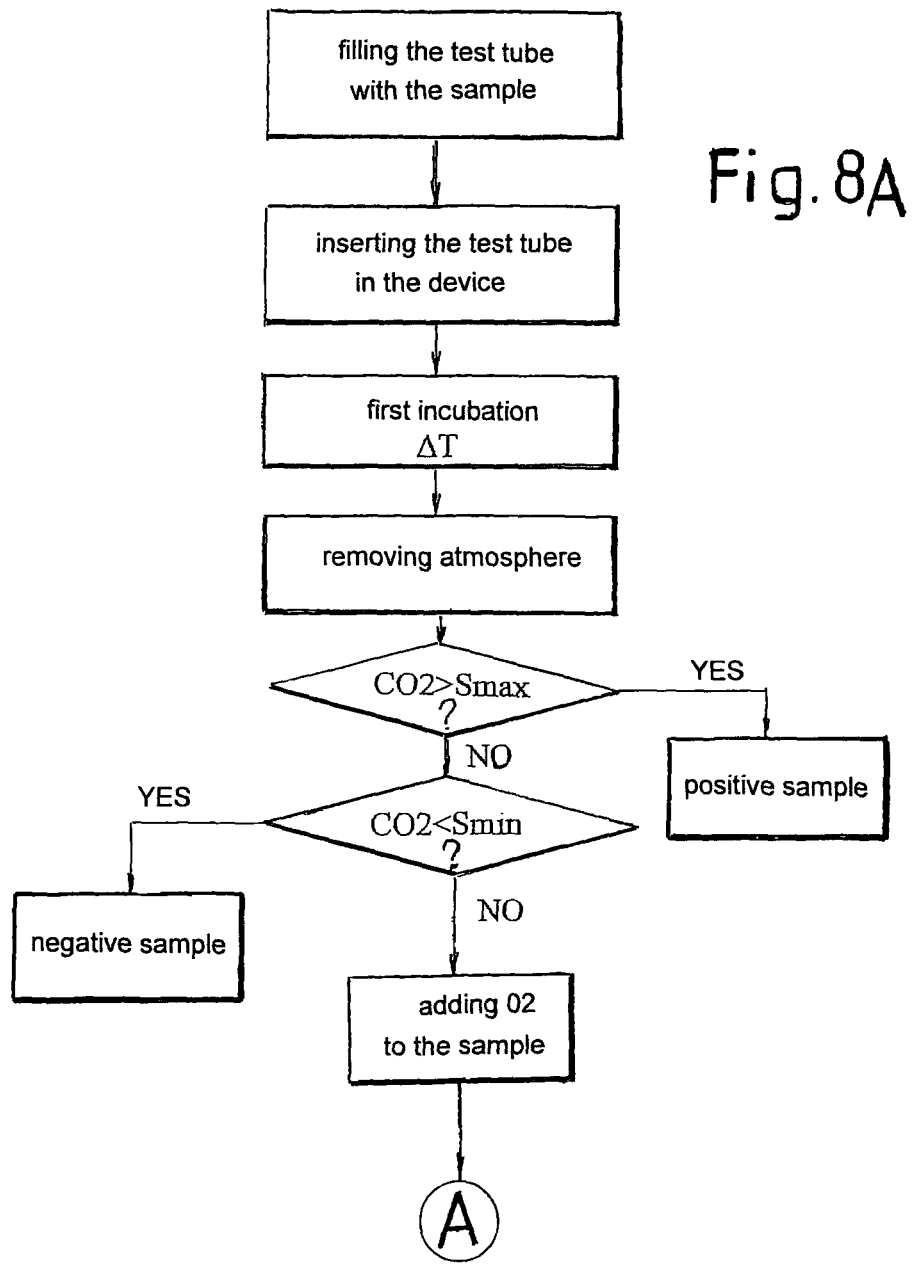
FIG. 8 shows a flow chart of the analysis method according to the present invention.

The entire process is schematically summarized in the flow chart of FIGS. 8A, 8B. The flow chart indicates how the single test tube is filled with the sample to be analyzed and then inserted in the device. Subsequently the test tube is subjected to incubation for a period $\Delta T$ and, once the incubation ended, the atmosphere from the test tube is removed. The detected carbon dioxide quantity is compared with a first threshold $S_{max}$ and a second threshold $S_{min}$. If the carbon dioxide content is greater than the threshold $S_{max}$ the sample is considered positive and discharged, by the sorter 15, through the well 65 in the space 51 below. If the carbon dioxide quantity is lower than the threshold $S_{min}$ the sample is considered negative and kept in the rack, and then it is ejected from the machine. If neither one or the other of the two conditions occurs, and thus the carbon dioxide content is comprised between $S_{max}$ and $S_{min}$, oxygen is added in the test tube to allow the prosecution of the metabolism and a second incubation is performed for a time interval that in this example lasts for a time $\Delta T$ equal to that of the first incubation, although this is not strictly necessary, a different duration for the two incubation phases being possible. Once the second incubation is ended, the atmosphere is removed from the test tube and the carbon dioxide content is compared with a single threshold, which in the illustrated example is the threshold $S_{max}$, but which may be equal to the threshold $S_{min}$ or to a threshold different from the thresholds $S_{max}$ and $S_{min}$. If the sample has developed a carbon dioxide quantity greater than $S_{max}$ it will be considered positive, otherwise it will be considered negative.

Figure 7:
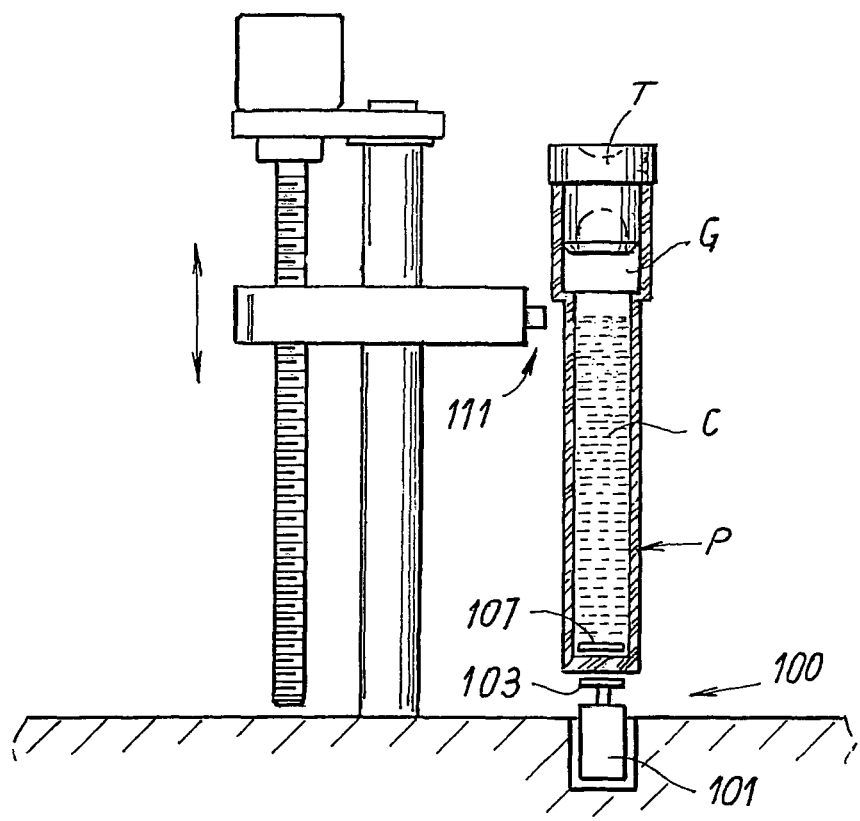
FIG. 7 shows a longitudinal section of a container with a magnetic agitating element and an outer agitator.

In order to optimize the incubation of the samples, according to some embodiments in the incubation area 7 agitating members are provided, positioned in an adequate manner along the feed path of the racks. These agitators are not shown in FIGS. 1 to 6 in order to simplify the drawing, but one of them is schematically represented in FIG. 7 below a single test tube P. The agitator of FIG. 7 is generically indicated with the number 100. It comprises an actuator 101, for example an electric motor, which puts in rotation a magnetic element 103, for example a magnetic bar inserted inside a disk keyed onto the shaft of the motor 101. The magnetic element 103 acts as a magnetic carrier for an agitating element 107 contained in the test tube P and drowned in the sample C, which is in the same test tube P. The magnetic coupling between the element 103 and the element 107 causes, due to the effect of the rotation of the shaft 101, the rotation of the element 107. This latter can be adequately shaped, for example with fins, to create a possible upwards movement of the sample C contained in the test tube P to optimize the incubation conditions thereof inside the test tube P, in which also the growth medium is contained.

FIG. 7 schematically shows also a further possible feature of the device according to the present invention, constituted by a sensor generically indicated with 111 and suitable to detect the level of the sample C inside the test tube P. The sensor 111 can be a capacitive sensor or a sensor of any other type. For example it can comprise an emitter/receiver device to detect the level of the sample C by transparency. The sensor 111 can be provided with a vertical movement parallel to the axis of the test tube P in order to detect the level of the sample C in the test tube. The sensor 111 can be arranged in any adequate position inside the device 1, for example in the free area between the load area 3 and the incubation area 7, as schematically indicated with 111 in FIG. 1, so as to determine the level of the sample in each single test tube during the transfer of the test tubes contained in the racks R performed by the transferring unit 1 from the loading area 3 to the incubation area 7.

Determining the level of the sample C in each test tube P allows avoiding the accidental immersion of the tip of the needles or cannulas 45 inside the biological sample, as this circumstance can damage the sensors 41A, 41B. The central control unit of the machine can store the level of the sample C detected in each test tube P so as to allow the lowering movement of the slide 47, which carries the needles 45, to be always sufficient to perforate the caps T of the test tubes P, but such that the needles do not come into contact with the sample.

With the method and the equipment described above it is possible to sort a high number of samples contained in test tubes P after a first incubation period (for example about one hour), sorting them into surely positive sample, surely negative samples and uncertain samples, if any. These latter can be considered positive for safety and simplicity, or they can be subjected to a second incubation cycle and thus to a second sorting between positive samples and negative samples according to a method schematically summarized in the flow chart of FIGS. 8A, 8B. Finally, independent of the method chosen, after a period of max. two hours it is possible to obtain from a high number of samples a first sure result on surely negative samples and a significant reduction of the samples which must be subjected to a longer and more accurate analysis, for example through seeding, to detect which microorganisms are there inside the samples classified as positive. Therefore, only these samples will be subjected to seeding or other analysis with a considerable saving in costs and risks.

This allows to obtain substantial advantages with respect to all the traditional methods of analysis, in particular those described in the patent documents mentioned in the introductory part of the present description.

In order to automate the analyses carried out by the device described above, it is possible to provide that the single test tubes P are marked in the production phase with a univocal code. Each test tube will be furthermore provided with a label, a band or the like, carrying a code, for example in the form of a bar code, connected in a bi-univocal manner to the data of the patient to whom the sample C contained in the test tube pertains. The equipment 1 can be provided with a bar code reader or the like, which reads the univocal code applied to the test tube in the production phase and the code related to the patient to whom the sample contained in the test tube belongs. These two codes are matched by the central unit of the equipment 1, so that the code related to the patient, applied for example by means of a band around the cap of the test tube P, can be subsequently removed in order to facilitate the analysis operations on the samples deemed positive. These analyses, for example seeding, in fact require the breakage of the test tube and thus the risk of damage to the bar code, which identifies the patient and is applied on the cap. The matching between code of the test tube and code of the patient, carried out by means of the reader associated to the device 1, avoids the risks of loss of the data of the patient to whom the sample belongs, when the test tube is broken to perform seeding.

Subsequent analysis operations are performed automatically, by storing the identification code of the test tube which matched in a one-to-one manner the patient code and associating the result of the analysis with the code of the test tube. Once the analyses have been performed and the result obtained, these can be matched again to the data of the patient simply recovering the data through the identification code of the patient and the identification code of the test tube mutually associated.

It is understood that the drawing only shows an example provided by way of a practical arrangement of the invention, which can vary in forms and arrangements without however departing from the scope of the concept underlying the invention. Any reference numbers in the appended claims are provided for the sole purpose of facilitating reading of the claims in the light of the description and the drawing, and do not in any manner limit the scope of protection represented by the claims.

The invention claimed is:

1. A method of biological analysis of biological samples, the method comprising the steps of:
    introducing a plurality of biological samples to be analyzed in a plurality of containers containing a growth medium;
    incubating the containers for a first incubation time interval;
    following said first incubation time interval, analyzing the atmosphere in said containers and comparing the atmosphere in said containers with a predetermined maximum value and a predetermined minimum value of carbon dioxide concentration;
    classifying said containers whose samples have an atmosphere containing a carbon dioxide quantity lower than the predetermined minimum value as not containing a pathologically relevant bacterial load;
    classifying said containers whose samples have an atmosphere containing a carbon dioxide quantity greater than the predetermined maximum value as containing a pathologically relevant bacterial load;
    separating said containers containing said pathologically relevant bacterial load from said containers not containing said pathologically relevant bacterial load via a sorter and collecting said samples containing said pathologically relevant bacterial load in a collection area, wherein said samples containing said pathologically relevant bacterial load are taken from said collection area and subjected to a further analysis to determine which microorganisms are present in said samples containing said pathologically relevant bacterial load;
    classifying said containers whose samples have an atmosphere containing a carbon dioxide quantity comprised between the predetermined maximum value and the predetermined minimum value as containing an uncertain sample;
    separating said containers containing said uncertain samples from said containers containing said pathologically relevant bacterial load and from said containers not containing said pathologically relevant bacterial load via said sorter;
    subjecting said containers containing said uncertain samples to a second incubation time interval after said containers containing said uncertain samples are injected with oxygen;
    at the end of said second incubation time interval, analyzing the atmosphere in said containers containing said uncertain samples and classifying said containers containing said uncertain samples as containing a pathologically relevant bacterial load or not containing a pathologically relevant bacterial load depending upon whether the carbon dioxide content in the atmosphere of the container is greater or lower than a threshold value, respectively;

subjecting said samples of said containers containing said pathologically relevant bacterial load to a further analysis to determine which microorganisms are present in the samples.

2. A method as claimed in claim 1, wherein if the biological sample is classified as containing a pathologically relevant bacterial load after the second time interval of incubation, the biological sample is subjected to an analysis in order to determine the microorganisms present, whilst if the biological sample is classified as not containing a pathologically relevant bacterial load no analysis is performed on said biological sample in order to determine the microorganisms present.

3. A method as claimed in claim 1, wherein during said first incubation time interval and during said second incubation time interval the biological sample is maintained in thermostatic conditions.

4. A method as claimed in claim 1, wherein during said first incubation time interval and during said second incubation time interval the biological sample is subjected to agitation.

5. A method as claimed in claim 1, wherein a plurality of biological samples are analyzed in sequence, and after said first incubation time interval the atmosphere in the container of each biological sample is analyzed and each biological sample is inserted in one of the following groups based upon the carbon dioxide content detected in said atmosphere:
   positive samples, which are subjected to a further analysis in order to detect the microorganisms present in the biological sample;
   negative samples, which are not subjected to the analysis for the detection of the microorganisms present;
   uncertain samples, which are subjected to a second incubation time interval, wherein the uncertain samples, after said second incubation, are subsequently classified in one of the following groups based upon the carbon dioxide content detected in the atmosphere of the respective container:
   positive samples, which are subjected to a further analysis in order to detect the microorganisms present in the biological sample;
   negative samples, which are not subjected to said analysis.

6. A method as claimed in claim 2, wherein during said first incubation time interval and during said second incubation time interval the biological sample is maintained in thermostatic conditions.

7. A method of biological analysis of biological samples, the method comprising the steps of:
   providing a sorter;
   providing an incubation area;
   providing a plurality of containers, each container comprising a biological sample and a growth medium;
   incubating said plurality of containers for an incubation time interval in said incubation area;
   measuring a carbon dioxide content in each of said plurality of containers after incubating said plurality of container for said first incubation time interval;
   determining a bacterial load of said plurality of containers after measuring said carbon dioxide content by comparing said carbon dioxide content of each of said plurality of containers with a predetermined maximum value of carbon dioxide concentration and a predetermined minimum value of carbon dioxide concentration;
   sorting said plurality of containers based on said bacterial load via said sorter such that each of said containers having said carbon dioxide content less than said predetermined minimum value is removed from said incubation area via said sorter and not subjected to further analysis and each of said containers having said carbon dioxide content greater than said predetermined maximum value is removed from said incubation area via said sorter, whereby said containers having said carbon dioxide content less than said predetermined minimum value are separated from said containers having said carbon dioxide content greater than said predetermined maximum value via said sorter, wherein containers having a carbon dioxide content between said predetermined maximum value and said predetermined minimum value are provided in said incubation area, said containers having said carbon dioxide content greater than said predetermined maximum value being subjected to further analysis to determine which microorganisms are present in each of said containers having said carbon dioxide content greater than said predetermined maximum value.

8. A method in accordance with claim 7, further comprising:
   delivering oxygen to one or more said containers in said incubation area when said carbon dioxide content of said one or more said containers is between said predetermined maximum value and said predetermined minimum value to provide one or more oxygen containing containers;
   incubating said one or more oxygen containing containers for another incubation time interval in said incubation area;
   determining said bacterial load of said one or more oxygen containing containers in said incubation area at an end of said second incubation time interval by comparing said carbon dioxide content of each of said one or more oxygen containing containers with a threshold carbon dioxide concentration value;
   sorting said one or more oxygen containing containers based on said bacterial load such that each of said one or more oxygen containing containers having said carbon dioxide content less than said threshold carbon dioxide concentration value is removed from said incubation area and not subjected to further analysis and each of said one or more oxygen containing containers having said carbon dioxide content greater than said threshold carbon dioxide concentration value is subjected to further analysis to determine which microorganisms are present in each of said one or more oxygen containing containers having said carbon dioxide content greater than said threshold carbon dioxide concentration value.

9. A method of biological analysis of biological samples, the method comprising the steps of:
   providing a plurality of containers comprising a growth medium and a biological sample to be analyzed;
   providing a sorter;
   providing a first incubation area;
   providing a second incubation area;
   incubating said containers for a first incubation time interval in said first incubation area;
   removing said containers from said first incubation area and determining a concentration of carbon dioxide in said containers after said first incubation time interval;
   comparing said concentration of carbon dioxide in said containers with a predetermined maximum value of carbon dioxide concentration and a predetermined minimum value of carbon dioxide concentration;
   categorizing each of said containers based on said comparison of said determined concentration of carbon dioxide and said predetermined maximum value and said predetermined minimum value as containing one of a pathologically relevant bacterial load, pathologically insignificant bacterial load and a pathologically load of unknown significance;

removing one or more said containers categorized as containing said pathologically insignificant bacterial load via said sorter such that said one or more containers categorized as containing said pathologically insignificant bacterial load is not subjected to further analysis, wherein one or more said containers categorized as containing pathologically relevant bacterial load is separated from said one or more said containers categorized as containing pathologically insignificant bacterial load via said sorter;

subjecting one or more said containers categorized as containing pathologically relevant bacterial load to further analysis to determine which microorganisms are present in said biological sample;

transferring one or more of said containers categorized as containing said pathologically load of unknown significance to said second incubation area, wherein said one or more said containers categorized as containing said pathologically load of unknown significance is separated from said one or more said containers categorized as containing pathologically relevant bacterial load and said one or more said containers categorized as containing pathologically insignificant bacterial load via said sorter; and incubating said one or more containers categorized as containing said pathologically load of unknown significance in said second incubation area for a second incubation time interval.

10. A method in accordance with claim 9, wherein said carbon dioxide concentration of said one or more containers categorized as containing said pathologically relevant bacterial load is greater than said predetermined maximum value of carbon dioxide concentration, said carbon dioxide concentration of said one or more containers categorized as containing said pathologically insignificant bacterial load being less than said predetermined minimum value of carbon dioxide concentration, said carbon dioxide concentration of said one or more containers categorized as containing pathologically load of unknown significance being between said predetermined minimum value of carbon dioxide concentration and said predetermined maximum value of carbon dioxide concentration.

11. A method in accordance with claim 10, further comprising:

providing oxygen to said one or more containers categorized as containing said pathologically load of unknown significance prior to incubating said one or more containers categorized as containing said pathologically load of unknown significance for said second incubation time interval to provide one or more oxygen containing containers;

determining whether said one or more oxygen containing containers comprises one of said pathologically significant bacterial load and said pathologically insignificant bacterial load at an end of said second incubation time interval by comparing said carbon dioxide concentration of said one or more oxygen containing containers with a threshold carbon dioxide concentration value, wherein said one or more oxygen containing containers is removed and not subject to further analysis when said carbon dioxide concentration of said one or more oxygen containing container is less than said threshold carbon dioxide concentration value, said one or more oxygen containing containers being subject to further analysis to determine which microorganisms are present in said one or more oxygen containing containers when said carbon dioxide concentration of said one or more oxygen containing containers is greater than said threshold carbon dioxide concentration value.

* * * * *